(12) United States Patent
Maruyama et al.

(10) Patent No.: US 11,593,734 B2
(45) Date of Patent: Feb. 28, 2023

(54) SYSTEM AND METHOD FOR MANAGEMENT AND SUPPORT OF WORKPLACE

(71) Applicant: Hitachi, Ltd., Tokyo (JP)

(72) Inventors: Nahoko Maruyama, Tokyo (JP); Yukinori Katagiri, Tokyo (JP)

(73) Assignee: HITACHI, LTD., Tokyo (JP)

( * ) Notice: Subject to any disclaimer, the term of this patent is extended or adjusted under 35 U.S.C. 154(b) by 24 days.

(21) Appl. No.: 17/276,913

(22) PCT Filed: Nov. 13, 2019

(86) PCT No.: PCT/JP2019/044464
§ 371 (c)(1),
(2) Date: Mar. 17, 2021

(87) PCT Pub. No.: WO2020/183793
PCT Pub. Date: Sep. 17, 2020

(65) Prior Publication Data
US 2021/0374639 A1    Dec. 2, 2021

(30) Foreign Application Priority Data

Mar. 14, 2019    (JP) .............................. JP2019-047271

(51) Int. Cl.
*G06Q 10/06* (2012.01)
*G06Q 10/0631* (2023.01)

(52) U.S. Cl.
CPC .............................. *G06Q 10/06313* (2013.01)

(58) Field of Classification Search
None
See application file for complete search history.

(56) References Cited

U.S. PATENT DOCUMENTS

| 4,331,953 A * | 5/1982 | Blevins ................ G08B 25/016 340/309.3 |
| 2006/0282021 A1* | 12/2006 | DeVaul ................ A61B 5/0205 600/595 |

(Continued)

FOREIGN PATENT DOCUMENTS

| CN | 109191791 A * | 1/2019 | ......... G06K 9/00248 |
| JP | 2001-067569 A | 3/2001 | |

(Continued)

OTHER PUBLICATIONS

Patel et al. "Trends in Workplace Wearable Technologies and Connected-Worker Solutions for Next-Generation Occupational Safety, Health, and Productivity" (https://onlinelibrary.wiley.com/doi/10.1002/aisy.202100099) (Year: 2021).*

(Continued)

*Primary Examiner* — Sujay Koneru
(74) *Attorney, Agent, or Firm* — Mattingly & Malur, PC (57) ABSTRACT

A system for management and support of a workplace includes: an input unit to acquire environmental factor information from environmental sensors in a workplace and physiological internal state information from biosensors attached to workers; a database including a first storage category to store physiological internal state information of a worker in association with environmental factor information with respect to each worker and a second storage category to store physiological internal state information of a worker in association with environmental factor information with respect to a worker regarded as experienced; a computing unit to compare physiological internal state information of a particular worker at the current time with information about the particular worker stored in the first storage category and information stored in the second storage category, judge the physiological internal state of the (Continued)

particular worker, and determine alert content; and an output unit to generate an alert to a worker.

10 Claims, 5 Drawing Sheets

(56) References Cited

U.S. PATENT DOCUMENTS

| | | | | |
|---|---|---|---|---|
| 2008/0175356 A1* | 7/2008 | Seidberg | ................ | G08B 25/08 379/45 |
| 2009/0254404 A1* | 10/2009 | Eggenberger | .......... | G06Q 10/06 705/7.14 |
| 2010/0277341 A1* | 11/2010 | Abraham, III | ........... | H04Q 9/00 340/870.01 |
| 2011/0245689 A1* | 10/2011 | Suzuki | .................. | A61B 5/024 600/483 |
| 2014/0278638 A1* | 9/2014 | Kreuzkamp | ..... | G06Q 10/06398 705/7.15 |
| 2014/0324466 A1* | 10/2014 | Wertzberger | .......... | G16H 10/60 705/2 |
| 2016/0007915 A1 | 1/2016 | Berka et al. | | |
| 2016/0051166 A1* | 2/2016 | Menzel | ................. | A61B 5/002 600/301 |
| 2016/0171423 A1* | 6/2016 | El-Shishiny | ....... | G06Q 50/2057 705/7.17 |
| 2017/0060118 A1 | 3/2017 | Yokochi | | |
| 2017/0140637 A1* | 5/2017 | Thurlow | ................ | G08B 25/10 |
| 2017/0303187 A1* | 10/2017 | Crouthamel | ............ | H04W 4/80 |
| 2017/0329908 A1* | 11/2017 | Braswell | ................ | G16H 40/20 |
| 2017/0372216 A1* | 12/2017 | Awiszus | ............... | A62B 18/006 |
| 2018/0192873 A1* | 7/2018 | Chausiaux | ........... | A61B 5/6831 |
| 2018/0334097 A1* | 11/2018 | Ishibashi | .................. | B60Q 9/00 |
| 2019/0362243 A1* | 11/2019 | Matsumura | ............ | G06Q 10/10 |
| 2021/0004764 A1* | 1/2021 | Matsumura | .......... | G05B 19/406 |
| 2021/0038077 A1* | 2/2021 | Nishida | ................ | A61B 3/1225 |
| 2021/0073096 A1* | 3/2021 | Kato | ...................... | B25J 9/1676 |
| 2021/0233654 A1* | 7/2021 | Arthur | ........... | G06Q 10/063114 |
| 2021/0350312 A1* | 11/2021 | Swift | ............... | G06Q 10/06313 |

FOREIGN PATENT DOCUMENTS

| | | |
|---|---|---|
| JP | 2009275789 A * | 11/2009 |
| JP | 2017-049818 A | 3/2017 |
| WO | 2018/070007 A1 | 4/2018 |

OTHER PUBLICATIONS

International Search Report of PCT/JP2019/044464 dated Feb. 4, 2020.

* cited by examiner

SYSTEM AND METHOD FOR MANAGEMENT AND SUPPORT OF WORKPLACE

TECHNICAL FIELD

The present invention pertains to a system for management and support of a workplace and particularly relates to a system and method for management and support of a workplace, taking account of human circumstances on physical and mental aspects of a worker.

BACKGROUND ART

In living a social life, people do some sort of work using a machine in an open or closed space. In the present invention, such space is defined as a workplace. For doing work smoothly in a workplace, it is important to take account of human circumstances on physical and mental aspects of a worker. For instance, if a worker engaged in work is not in good health or feels mental pressure because the worker is unfamiliar, it is required to take countermeasures such as replacing the worker with another worker or assigning an experienced worker to help the worker.

In this regard, for conventional systems for management and support of a workplace, their subject is giving consideration mainly from a perspective of following work process steps. In reality, these systems are far from a system for management and support of a workplace, taking account of human circumstances on physical and mental aspects of a worker.

Patent Literature 1 is known as an example in which a workplace is a vehicle and human circumstances on physical and mental aspects are taken into account. In Patent Literature 1, there is a description below: "a vehicle control device provided with a vehicle travel control unit that controls traveling of a vehicle, characterized by comprising an anxiety judgment unit to judge whether the vehicle driver is in an anxiety state based on biological information of the driver, a line of sight detection unit to detect the line of sight of the driver, a circumjacent object finding unit to detect circumjacent objects existing around the vehicle or in a blind spot, a unit for identifying an anxiety causing object to identify an object causing the driver to feel anxiety as one of the circumjacent objects detected by the circumjacent object finding unit, and a unit for determining a counteraction against anxiety to determine a counteraction that represents an operation of the vehicle to relieve the anxiety of the driver based on the anxiety causing object and provide the counteraction to the vehicle travel control unit."

CITATION LIST

Patent Literature

Patent Literature 1: WO2018/070007A1

SUMMARY OF INVENTION

Technical Problem

According to Patent Literature 1, in a workplace where autonomous driving of a vehicle is possible, it is successful to reduce burdens of the vehicle driver by detecting anxiety from the driver's line of sight and carrying out autonomous driving.

However, in a general workplace, it is reasonable to think that more diverse states occur in human circumstances beyond not only inferring human circumstances by analogy only from the line of sight. Also, in many cases, it is conceivable that a solution is not always made by reflection in machine control like autonomous driving.

From the above, the present invention is intended to provide a system and a method for management and support of a workplace and adapted to be applicable in a general workplace.

Solution to Problem

From the above, one aspect of the present invention resides in "a system for management and support of a workplace where workers and a machine exist, characterized by comprising an input unit to acquire environmental factor information from environmental sensors installed in a workplace and physiological internal state information from biosensors attached to workers; a database including a first storage category to store physiological internal state information of a worker in association with environmental factor information with respect to each worker and a second storage category to store physiological internal state information of a worker in association with environmental factor information with respect to a worker regarded as experienced; a computing unit to compare physiological internal state information of a particular worker at the current time with information about the particular worker stored in the first storage category and information stored in the second storage category, judge the physiological internal state of the particular worker, and determine alert content; and an output unit to generate an alert to a worker."

Another aspect of the present invention resides in "a method for management and support of a workplace where workers and a machine exist, characterized by comprising acquiring environmental factor information from environmental sensors installed in a workplace and physiological internal state information from biosensors attached to workers; storing physiological internal state information of a worker in association with environmental factor information with respect to each worker; storing physiological internal state information of a worker in association with environmental factor information with respect to a worker regarded as experienced; comparing physiological internal state information of a particular worker at the current time with stored information about the particular worker and stored information about the worker regarded as experienced, judging the physiological internal state of the particular worker, and generating an alert to a worker."

Advantageous Effects of Invention

According to the present invention, it is possible to provide a system for management and support of a workplace and adapted to be applicable in a general workplace.

DESCRIPTION OF EMBODIMENTS

In the following, embodiments of the present invention will be described in detail with reference to the drawings.

First Embodiment

Figure 1:
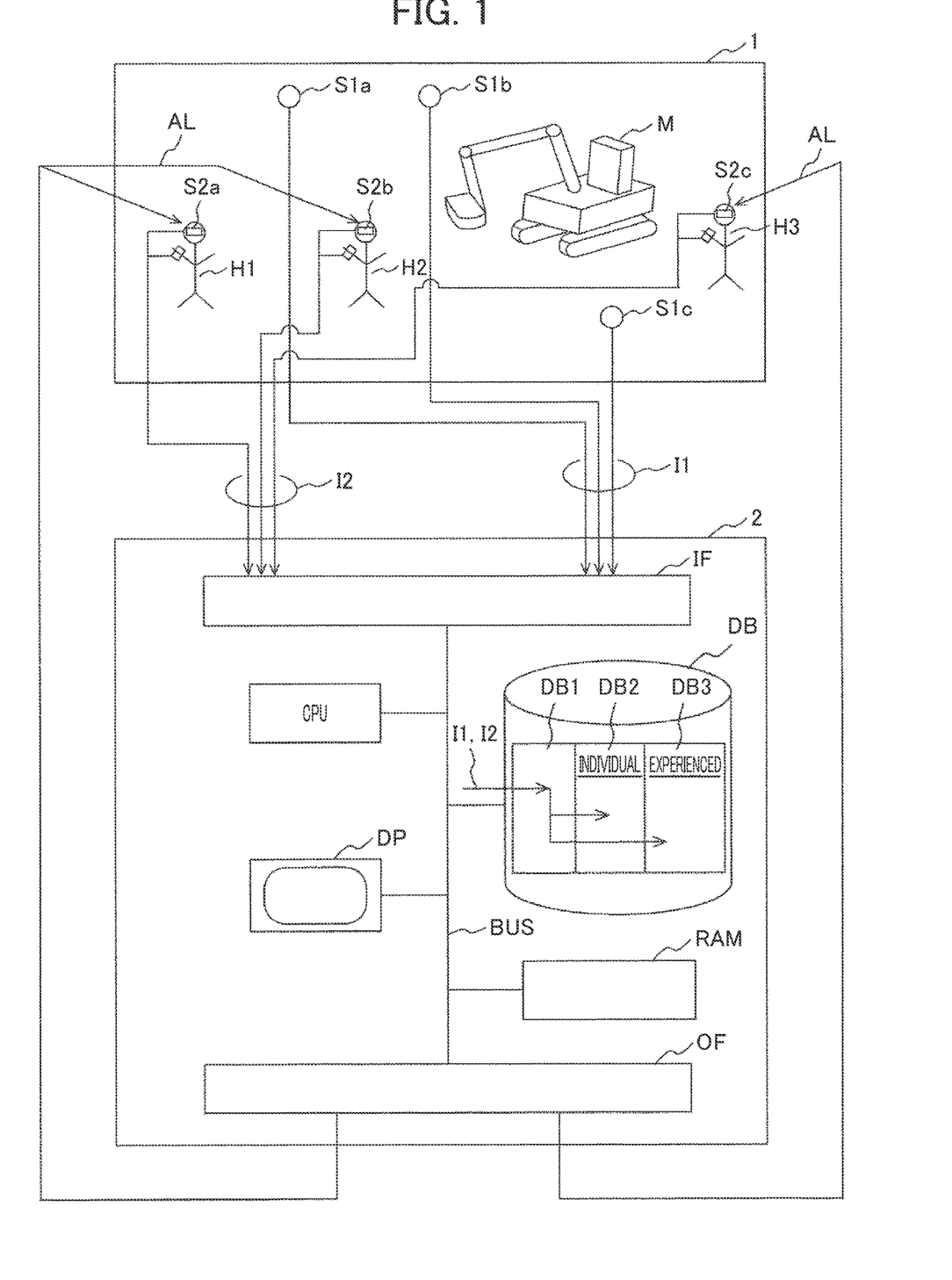
FIG. 1 is a diagram depicting an example of a configuration of a system for management and support of a workplace pertaining to a first embodiment of the present invention.

FIG. 1 depicts an example of a configuration of a system for management and support of a workplace pertaining to a first embodiment of the present invention.

In FIG. 1, a workplace 1 and a system 2 for management and support that is configured with a computer are depicted. Here, the workplace 1 may be either an open space such as an outdoor site or a closed space such as an indoor site and it is a place where a machine M and humans (workers) H (illustrated as H1, H2, and H3 in the drawing) perform some sort of work.

Also in the work place 1, environmental sensors S1 (illustrated as S1a, S1b, and Sic in the drawing) are installed and the workers H1, H2, and H3 wear biosensors S2 (illustrated as S2a, S2b, and S2c in the drawing), respectively.

Here, the environmental sensors S1 may be any sort of sensors to collect environmental information widely, such as a camera that overlooks the workplace 1 or keeps track of behavior of the workers and a sensor for weather conditions including temperature and humidity in the case of an outdoor workplace. Information detected by the environmental sensors S1 is referred herein to as environmental factor information I1. Here, m pieces of environmental factor information I1 are assumed to be acquired.

The biosensors S2 are sensors attached to, inter alia, the head or wrist of each worker H and measure a physiological internal state of each individual. In particular, inter alia, pulses that are obtained by a pulse rate monitor (including the number of beats, variation of interval (pNN50), and frequency (LF/HF)), brain waves that are acquired by an electroencephalograph (including $\alpha$ wave intensity, $\beta$ wave intensity, and ratio between $\alpha$ wave and $\beta$ wave), and movement of the line of sight that is obtained by an accelerometer or camera images (including a time during which the line of sight stays, eye speed, and frequency of movement of the line of sight) can be adopted. Information detected by the biosensors S2 is referred herein to as physiological internal state information I2. Here, n pieces of physiological internal state information I2 are assumed to be acquired.

Note that environmental factor information I1 and physiological internal state information I2 are not only a single piece of information that is directly acquired from a single sensor, also include information that is inferred by analogy using one or multiple sensors or information that is obtained by analysis of camera images or the like. Although environmental factor information I1 and physiological internal state information I2 are depicted in FIG. 1 as those that are created before being input to the computer 2, such information may be processed or combined within the computer.

Besides, environmental factor information I1 and physiological internal state information I2 are such that measurement values are linked with acquired time information. Particularly, physiological internal state information I2 as such with respect to each individual H1, H2, and H3 of the workers H for which physiological internal states were measured is linked with acquired time information.

The system 2 for management and support that is configured with the computer is comprised of, inter alia, an input unit IF, an output unit OF, a computing unit CPU, a database DB, and a display unit DP which are arranged along a bus BUS. Among them, the database DB retains environmental factor information I1 and physiological internal state information I2 taken in through the input unit IF or retains intermediate products and results of a computing process performed by the computing unit CPU.

In the first embodiment of the present invention, environmental factor information I1 and physiological internal state information I2 to be retained in the database DB are classified into three categories, sorted out, and retained. Latest information acquired by the sensors S1 and S2 is retained in a first category DB1 in the database DB.

Map information created from environmental factor information I1 and physiological internal state information I2 accumulated as past information is retained in a second category DB2 and a third category DB3 in the database DB. Between these, the second category DB2 retains map information created for each individual H1, H2, and H3 of the workers H and the third category DB3 retains map information created only for experienced workers.

Figure 2:
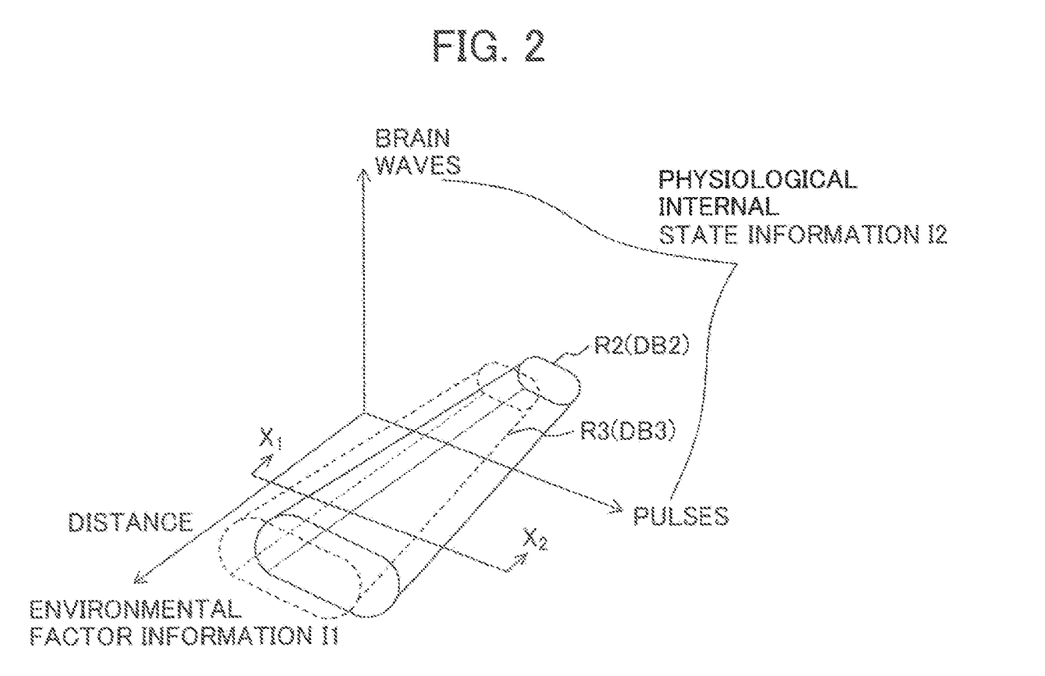
FIG. 2 is a diagram depicting a concrete example of schematized representation of map information retained in a second category DB2 and a third category DB3 in a database DB.

FIG. 2 depicts a concrete example of schematized representation of map information retained in the second category DB2 and third category DB3 in the database DB. Here is a three-dimensional display of map examples R2 and R3 created using three elements, brain waves and pulses which are taken out of the n pieces of physiological internal state information I2 and distance between a worker H and the machine M which is taken out of the m pieces of environmental factor information I1. Note that information of the distance between a worker H and the machine M can be obtained from image information acquired by a camera as one of the environmental sensors S1. Also, map examples can be displayed in any dimension and, in any case, are configured including environmental factor information I1 and physiological internal state information I2.

Here, a map example R2 is map information (retained in the second category DB2 in the database DB) specific to an individual (worker H3), created from environmental factor information I1 and physiological internal state information I2 accumulated as past information about, e.g., a worker H3. A map example R3 is map information (retained in the third category DB3 in the database DB) suitable for an environment, created from environmental factor information I1 and physiological internal state information I2 accumulated as past information about an experienced worker.

Such map information has significance in indicating that, typically, as a worker H gets closer to the operating machine M, the degree of his or her tension increases and this appears in brain waves and pulses. Note that, in particular, the following, plotted on a graph, can be used as indexes of the degree of tension: as for brain waves, height of frequency appearing ($\beta$ wave has a higher ratio than $\alpha$ wave); as for pulses, less variation of beat interval (a smaller value of pNN50); high proportion of a low frequency power spectrum (a larger value of LF/HF) resulting from a frequency analysis of pulses; and so on. It is indicated that the degree of tension of an unexperienced worker H3 is higher than that of an experienced worker. According to data reflecting a great number of experiences accumulated in the past, there is a distinct difference between each individual worker and an experienced worker in terms of both human and environmental aspects, as in FIG. 2.

In the present invention, a region of an experienced worker drawn with dashed lines in FIG. 2 is judged as an ideal condition in a sense and this region is judged as a physiological internal state map fit for an environment. Also, a region drawn with solid lines, which corresponds to a map of an individual worker who is compared with an experienced worker, is regarded as a physiological internal state map specific to a worker (user).

Figure 3:
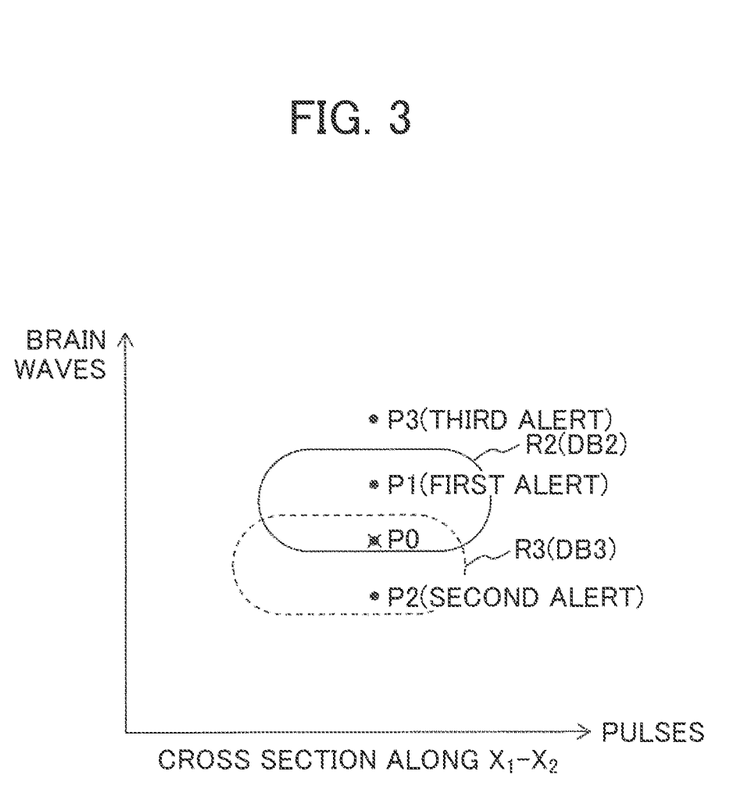
FIG. 3 is a diagram representing the current condition of an unexperienced worker in comparison with the condition of an experienced worker.

Furthermore, for an unexperienced worker H3 in FIG. 2, let us try to display his or her latest condition through reference to information retained in the first category DB1 in the database DB. When, for example, a plane based on the latest environmental factor information I1 is a cross section along X1-X2, a map in the latest environment can be considered as displayed in FIG. 3. FIG. 3 represents the current condition of the unexperienced worker H3 as the physiological internal state specific to the worker H3 and in comparison with the condition of an experienced worker.

In the present invention, after thus grasping the condition of a worker, a decision is made as below. First, suppose that a point P0 is indicative of the worker's latest condition. Because the point P0 falls within a region or a condition that corresponds to an ideal physiological internal state map of an experienced worker (his or her physiological internal state is fit for an environment), it is decided that the worker H3 is placed in a very stable normal mode today or at the current time.

Then, suppose that a point P1 is indicative of the worker's latest condition. Because the point P1 indicates an almost normal condition of the worker H3, but falls outside the region of an experienced worker, it is decided that the worker H3 is placed in a first alert mode today or at the current time. In this condition, as compared with an experienced worker, "the worker H3 may be careless, vague, or pressed for time" and "may be easy to make mistakes". Therefore, in the first alert mode, it is expedient that the system for management and support performs the following action: continuous monitoring of the worker H3, calling attention to the worker, or presenting operation support information to the worker among others. However, in the first alert mode, it is expedient to change such action (strictness), while seeing how many mistakes to make during monitoring usual behavior of the worker H3.

Then, suppose that a point P2 is indicative of the worker's latest condition. Because the point P2 falls within the region R3 of an experienced worker, but falls outside the region R2 of the worker H3, it is decided that the worker H3 is placed in a second alert mode today or at the current time. It is judged problematic that the worker's condition is extraordinary stable than usual. In the second alert mode, it is expedient that the system for management and support performs the following action: continuous monitoring of the worker H3, calling attention to the worker, or presenting operation support information to the worker among others. However, it is expedient that a stricter action should be performed, as the point P2 goes farther away from the user-specific region R2 of the worker H3.

Then, suppose that a point P3 is indicative of the worker's latest condition. Because the point P3 indicates the condition of the worker H3 deviating from his or her normal condition and falls outside the region of an experienced worker, it is decided that the worker H3 is placed in a third alert mode today or at the current time. In the third alert mode, it is expedient that the system for management and support performs the following action: continuous monitoring of the worker H3 or calling attention to the worker and, additionally, calling attention to a third person. It is expedient that a stricter action should be performed, as the point P3 goes farther away from the user-specific region R2 of the map of the worker H3.

Note that, in diverse alert modes described above, an alert is sent from the output unit OF in FIG. 1 to a worker H or appropriately displayed on the display DP. An alert AL is conveyed to a worker via a receiving unit worn by each individual worker. In this regard, if a worker uses AR glasses, an alert may be displayed within the field of view of the AR glasses as AR information, such as "you appear to be pressed for time. Be careful: first alert mode", "a display of a position to watch out for in the workplace: second alert mode", or "Caution. It is more likely to make mistakes: third alert mode" among others.

A method of the first embodiment noted above is, in short, to support an unexperienced worker or detect that a worker is placed in a physiological internal state inappropriate for work. If a worker in the workplace is not in a proper physiological internal state (the worker is unnecessarily nervous or vague among others), the method is to decide that the worker is placed in an alert mode and perform an action such as calling attention to the worker.

Note that, for execution of processing noted above, it is expedient to do as follows. First, the map example R2 (map information created from environmental factor information I1 and physiological internal state information I2 accumulated as past information about the worker H3) is physiological internal state information specific to a user. As regards acquiring this information, it is expedient to create this map using data acquired during training of the worker H3 who is the user. Subsequently, it is expedient to modify the map based on physiological internal state information during actual work acquired every fixed period.

Besides, as regards acquiring information for the map example R3 (physiological internal state information suitable for an environment with regard to an experienced worker), if it is difficult to define an experienced worker because the current equipment and work are new, physiological internal state information of a worker engaged in similar equipment and work can be used. Note that, as to who is regarded as an experienced worker among a lot of workers and whose map information is to be retained in the third category DB3 in the database DB, it is required to make an appropriate decision and setting. It is desirable that multiple workers are regarded as experienced and data to be retained in the third category DB3 grows.

In consideration of a process in which a worker is becoming proficient in unfamiliar work, after an experienced worker begins to work for new equipment and work content, his or her physiological internal state information should be acquired every fixed period and used as physiological internal state information fit for an environment when another worker begins to work for the equipment and work content.

Figure 4:
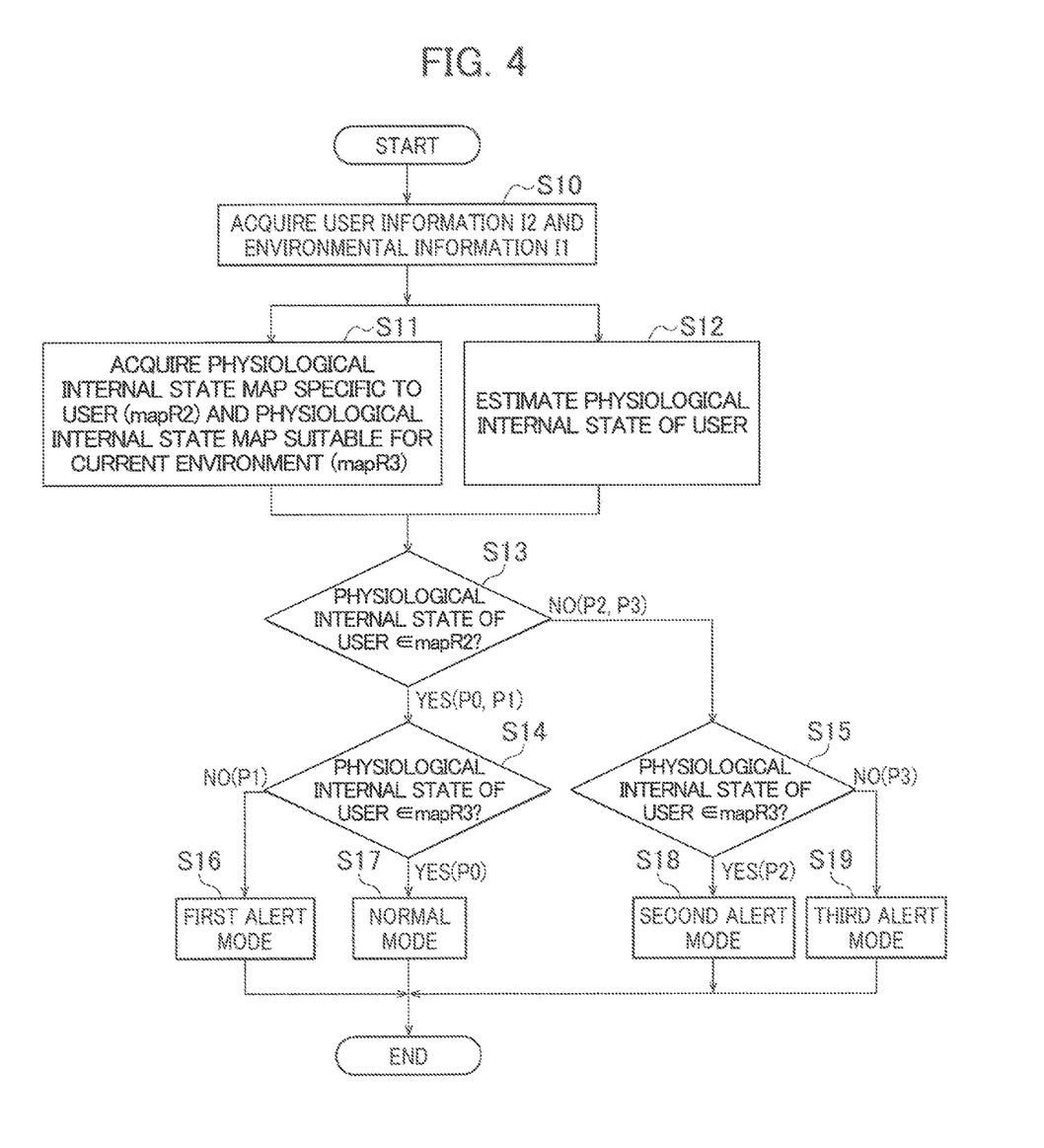
FIG. 4 is a diagram illustrating a flowchart of processing by the system for management and support of a workplace pertaining to the first embodiment.

FIG. 4 illustrates a flowchart of processing noted above that is performed by the computing unit CPU in FIG. 1. First, processing step S10 is to acquire user information (physiological internal state information I2) and environmental information (environmental factor information I1). The result of this step is retained in the database DB and the amount of data retained in the second category DB2 and third category DB3 grows over time. It follows that information that better reflects the physiological internal states of individual workers or reflects an ideal physiological internal state suitable for an environment is created and stored as maps like the map examples R2 and R3. Here, processing is described on the assumption that a sufficient amount of information exits in each category.

Processing step S11 is to acquire a physiological internal state map specific to a user (like the map example R2) retained in the second category DB2 and a physiological internal state map suitable for an environment (like the map example R3) retained in the third category DB3. On the other hand, processing step S12 is to estimate the physiological internal state of a user at the current time. This means retrieving the user's latest information acquired by the sensors S1 and S3 from the first category DB1 in the database DB.

Processing steps S13, S14, and S15 are to make decisions based on the regions in FIG. 3. Depending on the decisions in combination, each of processing steps S16 thru S19 is to determine a mode according to the applicable condition and give an external output.

According to the first embodiment, it is possible to provide a system for management and support of a workplace and adapted to be applicable in a general workplace.

Second Embodiment

In a second embodiment, descriptions are provided about how the system for management and support of a workplace should work when dispatching a suitable support person to cope with trouble occurring in a workplace.

In the second embodiment, it is assumed that automation equipment in a workplace (factory) falls into a situation where it is difficult to deal with and information corresponding to a request for support by a person whose physiological internal state is proper is issued from the automation equipment to the system for management and support. In this case, the following scene is assumed: as a few persons patrol for support of a process on an advanced automation line, they find that, e.g., an automatic packing robot places a product in a wrong orientation and cannot return the product correctly by itself and have to call for help by a person whose physiological internal state is as proper as possible.

In this case, support request information is given from the automation equipment to the system 2 for management and support of the workplace. Then, processing is performed by the computing unit CPU of the system 2 for management and support according to a flowchart in FIG. 5.

Figure 5:
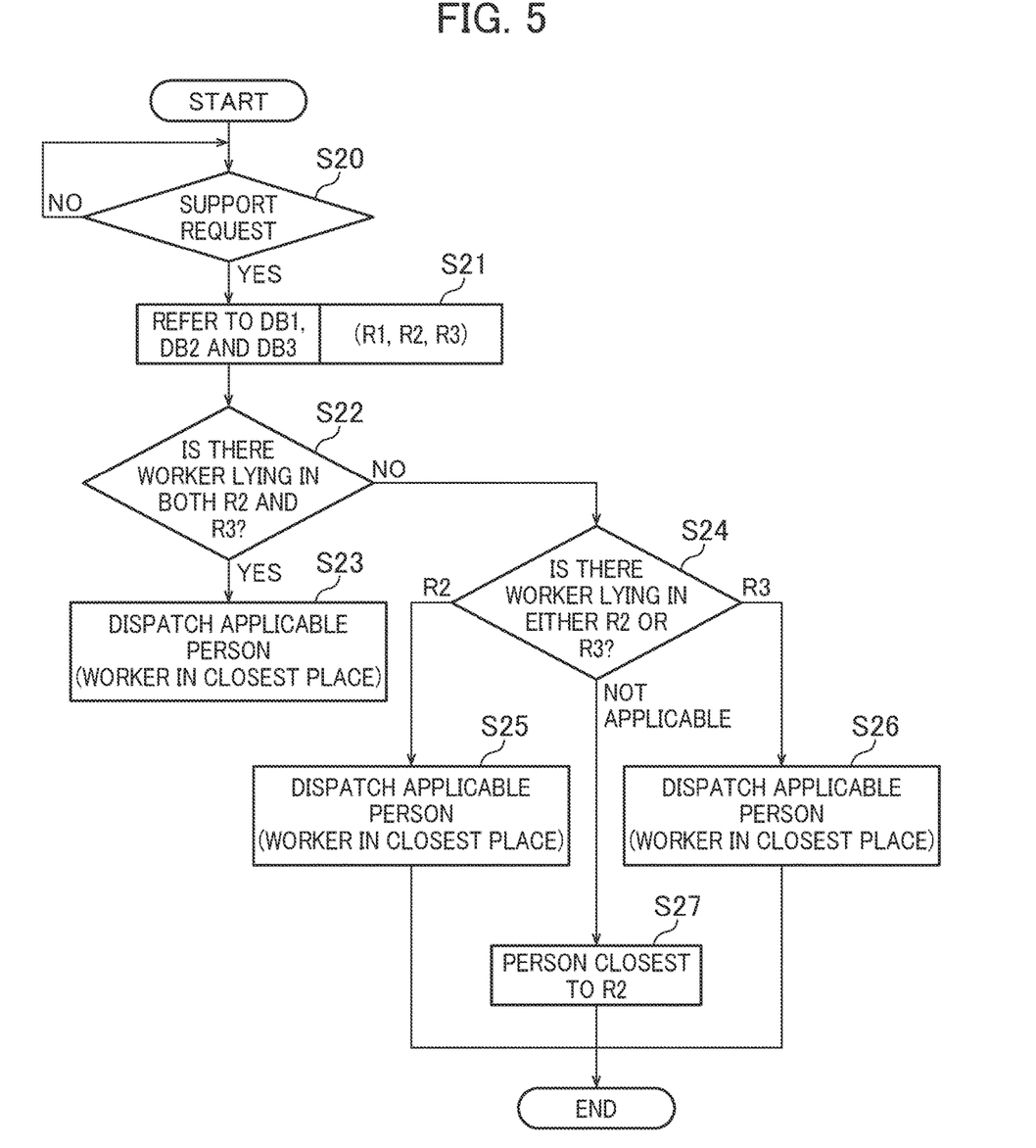
FIG. 5 is a diagram illustrating a flowchart of processing by the system for management and support of a workplace pertaining to a second embodiment.

As a result of decision at processing step S20, when a support request has been issued from the automation equipment, a transition is made to processing step S21 where reference is made to the first category DB1, second category DB2, and third category DB3 in the database DB.

Processing step S22 is to search for a worker whose physiological internal state is such that his or her current physiological internal state (in the first category DB1) lies in both the region R3 of the physiological internal state fit for an environment (in the third category DB3) and the region R2 of the physiological internal state specific to a user (in the second category DB3). This is checking a worker H1 to see whether the current condition of the worker H1 falls within the map region R2 of the worker H1 and also within the map region R3 of an experienced worker and checking all workers likewise. As a result, if there are multiple workers satisfying this condition, processing step S23 is to dispatch an applicable person for which the region R2 is closest to the region R3 to an abnormality occurrence location.

If there is no worker satisfying the condition (falling within both the regions R2 and R3), as decided at processing step S22, processing step S24 is to search for a worker whose physiological internal state lies in either the region R3 of the physiological internal state fit for an environment or the region R2 of the physiological internal state specific to a user. Processing step S25 or processing step S26 is to dispatch an applicable person falling in either of the regions. Additionally, if there are only workers that do not lie in both the regions, processing step S27 is to dispatch a person whose condition is closest to the region R2 of the physiological internal state specific to a user.

In the second embodiment noted above, in case of emergency in a workplace, when another person has to be selected and assigned to cope with the emergency, an optimal person is selected through reference to the regions of the physiological internal states. Thereby, in response to emergency, it is possible to dispatch a person who can cope with the emergency in relatively short order.

Third Embodiment

In a third embodiment, descriptions are provided about what the system for management and support of a workplace performs to handle a worker who is not aware of danger (not understanding or lacking in attention to danger) in a workplace.

This assumes the following scene: in a site where, e.g., a construction machine for drilling resources or the like is operated automatically, when a worker is relaxed in a position on the extension of the movement line of automatic machine operation, an alert is issued to the worker.

In the above example, the system for management and support is applied as follows: in a workplace where the spot to do work and the arrangement of things are changed in order, it is expedient to generate an alert to a dangerous object specified in advance, using a relationship between distance to the dangerous object and a physiological internal state, depicted in FIG. 2. Note that the system may be applied for a factory where layout is unchanged and, in this application, positional information within the factory may be used as environmental factor information, instead of a dangerous object. It is only required that the system can make a decision as to, inter alia, whether a person can have an appropriate sense of tension to a dangerous spot. To do more conveniently, such decision may be based on comparison between or among physiological internal states obtained per spot.

LIST OF REFERENCE SIGNS

1: workplace, 2: system for management and support, AL: alert, BUS: bus, CPU: computing unit, DB: database, DB1: first category in the database DB, DB2: second category in the database DB, DB3: third category in the database DB, DP: display unit, H1, H2, H3: workers, I1: environmental factor information, I2: physiological internal state information, IF: input unit, M: machine, OF: output unit, S1: environmental sensors, S2: biosensors

The invention claimed is:

1. A system for management and support of a workplace where workers and a machine exist, comprising:
a plurality of environmental sensors installed in the workplace, the environmental sensors including at least a camera;
a plurality of biosensors attached to the workers; and
a computer, the computer configured to:

acquire environmental factor information from the environmental sensors and acquire physiological internal state information from the biosensors;

a database coupled to the computer, the database storing physiological internal state information of a worker in association with environmental factor information with respect to each worker in a first storage category and storing physiological internal state information of an experienced worker in association with environmental factor information of the environment of the experienced worker, wherein the computer is configured to:

generate a three-dimensional map having a first axis representing a brain wave, a second axis representing a heart pulse and a third axis representing a distance from the particular worker to the machine, the three dimensional map including a first region of brain wave and heart pulse information based on physiological internal state information of the particular worker from the first storage category, a second region of brain wave and heart pulse information based on physiological internal state information of the experienced worker from the second storage category, the three-dimensional map further indicating a distance to the machine, compare physiological internal state information of the particular worker at a first time stored in the first storage category with physiological internal state information of the experienced worker stored in the second storage category, judge, based on the comparison, the physiological internal state of the particular worker, and determine, based on the comparison, alert content, generate and output an alert corresponding to the alert content to a worker, and display the generated three-dimensional map.

2. The system for management and support of a workplace according to claim 1, wherein the first time is a current time.

3. The system for management and support of a workplace according to claim 1, wherein the computer is configured to receive a request for dispatching a person to cope with trouble that has occurred in a workplace, refer to the database, and determine a person suitable for the dispatching.

4. The system for management and support of a workplace according to claim 1, wherein the computer is configured to judge a positional relation between a dangerous object and a respective worker in a workplace, refer to the database, and determine alert content to the worker.

5. The system for management and support of a workplace according to claim 2, wherein the computer is configured to receive a request for dispatching a person to cope with trouble that has occurred in a workplace, refer to the database, and determine a person suitable for the dispatching.

6. The system for management and support of a workplace according to claim 2, wherein the computer is configured to judge a positional relation between a dangerous object and a worker in a workplace, refer to the database, and determine alert content to the worker.

7. The system for management and support of a workplace according to claim 3, wherein the computer is configured to judge a positional relation between a dangerous object and a worker in a workplace, refer to the database, and determine alert content to the worker.

8. A method for a system of management and support of a workplace where workers and a machine exist, the system comprising: a plurality of environmental sensors installed in the workplace, the environmental sensors including at least a camera; and a plurality of biosensors attached to the workers, the method comprising:

acquiring environmental factor information from the environmental sensors and physiological internal state information from the biosensors;

storing physiological internal state information of a worker in association with environmental factor information with respect to each worker in a first storage category;

storing physiological internal state information of an experienced a worker in association with environmental factor information of the environment of the experienced worker;

generating a three-dimensional map having a first axis representing a brain wave, a second axis representing a heart pulse and a third axis representing a distance from the particular worker to the machine, the three dimensional map including a first region of brain wave and heart pulse information based on physiological internal state information of the particular worker from the first storage category, a second region of brain wave and heart pulse information based on physiological internal state information of the experienced worker from the second storage category, the three-dimensional map further indicating a distance to the machine;

comparing physiological internal state information of the particular worker at a first time stored in the first storage category with physiological internal state information of the experienced worker stored in the second storage category, judging, based on the comparison, the physiological internal state of the particular worker;

determining, based on the comparison, alert content; and generating an alert corresponding to the alert content to a worker.

9. The method for management and support of a workplace according to claim 8, wherein the first time is a current time.

10. The method for management and support of a workplace according to claim 9, further comprising the step of: determining whether, at the first time, the first region is within or outside the second region, and alert content is determined based on the determination.

* * * * *